(12) United States Patent
El Shafei et al.

(10) Patent No.: US 7,998,103 B2
(45) Date of Patent: Aug. 16, 2011

(54) DEVICE FOR IMPLANTATION OF RETROGRADE VENTRICULO-SINUS SHUNT

(76) Inventors: Ismail Lotfy El Shafei, Cairo (EG); Hassan Ismail El Shafei, Cairo (EG)

( * ) Notice: Subject to any disclaimer, the term of this patent is extended or adjusted under 35 U.S.C. 154(b) by 402 days.

(21) Appl. No.: 12/314,667

(22) Filed: Dec. 15, 2008

(65) Prior Publication Data
US 2009/0137942 A1    May 28, 2009

(51) Int. Cl.
*A61M 5/00* (2006.01)

(52) U.S. Cl. ............................................. 604/8

(58) Field of Classification Search ............. 604/8, 9
See application file for complete search history.

(56) References Cited

U.S. PATENT DOCUMENTS

| | | | | |
|---|---|---|---|---|
| 2,969,066 | A * | 1/1961 | Holter et al. | 604/9 |
| 3,020,913 | A | 2/1962 | Heyer | |
| 3,288,142 | A | 11/1966 | Hakim | |
| 3,769,981 | A | 11/1973 | Schults | |
| 5,385,541 | A * | 1/1995 | Kirsch et al. | 604/8 |
| 5,405,316 | A * | 4/1995 | Magram | 604/8 |
| 6,283,934 | B1 | 9/2001 | Børgesen | |

OTHER PUBLICATIONS

Ismail L. El Shafei, et al., "Ventriculo-Jugular Shunt Against the Direction of Blood Flow, I. Role of the Internal Jugular Vein as an Antisiphonage Device", Childs Nervous System, 3:282-284 (1987).

A. L Noordergraaf, Circulatory System Dynamics, Ch. 5, (1978).
W.L. McCabe, J.C. Smith, Unit Operations of Chemical Engineering, 2nd Edition, Ch. 3 "Fluid-flow Phenomena", (1967) pp. 47-67.
Ismail L. El-Shafei and Mahmound A El-Rifaii, "Ventriculo-jugular shunt against the direction of blood flow. II Theoretical and experimental basis for shunting the cerebrospinal fluid against the direction of blood flow", Child's Nervous System, (1987) 3:285-291.
Azza Mohamed Abdel Hamid El Shaarawy, "Study of Alternative Methods for Cerebrospinal Fluid Shunting to the Venous Circulation. Experimental Modeling". Thesis submitted to the faculty of Engineering at Cairo University in partial fulfillment of the requirements for the degree of Doctor of Philosophy in Chemical Engineering, Mar. 1997.
Ismail L. El Shafei, "Ventriculo-jugular shunt against the direction of blood flow, III Operative technique and results", Child's Nervous System, (1987) 3: 342-349.

(Continued)

Primary Examiner — Leslie Deak (57) ABSTRACT

A shunt system for implantation of retrograde ventriculo-sinus shunts to establish a water tight connection that drains excess cerebrospinal fluid from hydrocephalic brain ventricles and delivers it, against the direction of blood flow, in a dural sinus comprising a valveless shunting catheter and a styforator. Retrograde ventriculo-sinus shunts mimic natural drainage of cerebrospinal fluid; they utilize natural forces to regulate the intraventricular pressure and to maintain it more than the sinus pressure, to prevent regurgitation of blood in the shunting catheter as a result of changes in posture or intra-thoracic pressure, to maintain a steady flow of cerebrospinal fluid to the venous circulation at a rate equal to and dependent upon the rate of it's formation, to discourage stagnation and clotting of blood at the venous end of the connection and to prevent siphonage in the erect posture.

2 Claims, 4 Drawing Sheets

OTHER PUBLICATIONS

Ismail El Shafei and Mohamed Hafez, "Ventriculo-jugular shunt against the direction of blood flow, IV Technical modifications and policy for treatment", Child's Nervous system (1991) 7:197-204.

El Shafei IL, El Shafei HI, The retrograde ventriculo-sinus shunt. Concept and technique for treatment of hydrocephalus by shunting the cerebrospinal fluid to the superior sagittal sinus againt the direction of blood flow. Preliminary report. Child's nervous system (2001) 17:456-465.

Ismail L El Shafei, Hassan I El SHafei, "The retrograde ventriculo-sinus shunt (El Shafei RVS Shunt). Rationale, Evolution, Surgical technique and long term results." Pediatric Neurosurgery 2005;41:305-317.

* cited by examiner

DEVICE FOR IMPLANTATION OF RETROGRADE VENTRICULO-SINUS SHUNT

FIELD OF THE INVENTION

This invention relates generally to the surgical arts, more particularly, the present invention relates to shunt systems for the treatment of hydrocephalus.

Examples of shunt systems for the treatment of hydrocephalus are found in U.S. Pat. No. 2,969,066 issued to John. W. Holter and Eugene B. Spitz on Jan. 24, 1961 entitled "Device For Draining Ventricular Fluid In Cases Of Hydrocephalus", U.S. Pat. No. 3,020,913 issued to William T. Heyer on Feb. 13, 1962 entitled "Surgical Drain", U.S. Pat. No. 3,288,142 issued to S. Hakim on Nov. 29, 1966 entitled "Hydrocephalus Shunt With Spring Biased One-Way Valves", U.S. Pat. No. 3,769,981 issued to Rudolf R. Schults on Nov. 6, 1973 entitled "Physiological Drainage System With Closure Means Responsive To Downstream Suction", and U.S. Pat. No. 6,283,934B1 issued to Svend Erik Bergesen on Sep. 4, 2001 entitled "Device For The Treatment Of Hydrocephalus".

BACKGROUND OF THE INVENTION

1. Description of Related Art

In the medical arts, to relieve undesirable accumulation of fluids, it is frequently necessary to provide a means for draining a fluid from one part of the human body to another in a controlled manner. This is required, for example, in the treatment of hydrocephalus, an ailment usually afflicting infants or children in which cerebrospinal fluid accumulates within the skull and exerts pressure and skull deforming forces. The aim of treatment in hydrocephalus is to return the excess cerebrospinal fluid accumulating in the brain ventricles back to the venous circulation. This is done either directly by shunting it to the venous circulation, or indirectly by shunting it to a cavity, like the peritoneal cavity, from where it is absorbed into the venous circulation. This is typically done utilizing a drainage or shunt system including a catheter inserted into the brain ventricle through the skull which is connected to a tube that conducts the cerebrospinal fluid away from the brain to be introduced either into the peritoneal cavity, i.e. a ventriculo-peritoneal shunt system, or into the venous circulation by extending the distal catheter through the patient's internal jugular vein to the atrium portion of the heart, i.e. a ventriculo-atrial shunt system. After implantation of such shunt systems, two major problems are encountered: siphonage and thrombo-embolic complications.

Siphonage inevitably occurs whenever the patient assumes an upright posture regardless of the shunt system used. Siphonage develops whenever the ventricular catheter inlet, which is inside the skull, is elevated with respect to the distal catheter outlet, which is in the peritoneal cavity or the right atrium, i.e. when the patient sits, stands or is held erect. This siphonage effect occurs as a result of the hydrostatic pressure of the cerebrospinal fluid column in the vertical segment of the shunting catheter and causes cerebrospinal fluid overdrainage. Over-drainage of the cerebrospinal fluid causes excessive reduction of the cerebrospinal fluid pressure within the brain ventricles and predispose for the development of several complications, e.g., subdural hematomas and hygromas, overriding of the cranial bones and premature union of the skull bones in infants, excessive reduction of the ventricular size leading to the slit ventricle syndrome and shunt obstruction due to suction of choroid plexus or brain debris or due to impingement of the ventricular walls on the inlet holes of the ventricular catheter . . . etc. Furthermore, when a patient assumes the recumbent position after a period of over drainage in the upright position, cerebrospinal fluid flow to draining site stops completely until the intra-ventricular pressure builds up again; in effect, flow of cerebrospinal fluid to the drainage sites after implantation of current shunts is intermittent according to changes in posture or intra-thoracic pressure. Intermittent flow of the fluid predisposes to shunt obstruction and infection as a result of stagnation of the cerebrospinal fluid or reflux of blood into the shunting catheter. To sum up, siphonage is responsible, either directly or indirectly, for most of the problems and complications encountered after implantation of current shunts.

The thrombo-embolic complications, which are particularly peculiar to ventriculo-venous shunts, occur as a result of clotting of blood at the venous end of the connection. These are serious, fatal complications and because they are difficult to treat, ventriculo-atrial shunts are rarely implanted nowadays. The ventriculo-peritoneal shunt is the one most commonly used for the treatment of hydrocephalus.

Fluid flow control devices are incorporated into the shunt systems used for treatment of hydrocephalus, with the aim of maintaining a normal intra-ventricular pressure, prevention of siphonage in the upright body position and prevention of reflux of fluids into the shunt system. These devices are combinations of check valves, differential pressure valves and anti-siphonage devices. Although incorporation of these devices into shunt systems have improved the results, yet they are still far from satisfactory. Complications still occur frequently, the incidence of shunt revision is still high and the search to find solutions for the problems encountered after implantation of current shunt systems continues.

2. Evolution of the Concept of Treating Hydrocephalus by Implanting Retrograde Ventriculo-Sinus Shunts The concept of treating hydrocephalus by implanting retrograde ventriculo-sinus shunts, i.e. by establishing a water tight connection to drain excess cerebrospinal fluid accumulating in hydrocephalic ventricles and to deliver it into a dural sinus against the direction of blood flow in the sinus, evolved from two theoretical conclusions. The first conclusion addressed the problem of siphonage and the second conclusion addressed the problems of regulation of cerebrospinal fluid flow to the venous circulation, normalization of the intraventricular pressure, prevention of reflux of blood and prevention of blood clotting at the venous end of a ventriculovenous connection.

First Conclusion

The first conclusion was based on the fact that veins are collapsible tubes. The observation that veins may collapse in vivo is an old one and has traditionally been attributed to the fact that their walls are too thin to withstand even minor changes in their transmural pressure (N.B. Transmural pressure is the pressure inside the vein minus the ambient pressure). Since the pressure in the big veins in the body oscillates around a value close to atmospheric pressure, conditions under which transmural pressure drops below the zero level may prevail; investigators suggested that collapse of veins may play a role in regulation of the venous flow [A. L. Noordergraaf, Circulatory System Dynamics, Ch. 5, (1978)]. The internal jugular vein is the only segment in the venous channels that convey the venous blood from the brain to the heart which is exposed to the atmospheric pressure. In the recumbent position the vein lies in a horizontal plane, it's transmural pressure is just positive and it's contour is oval or even flat. During change of posture form recumbent to erect, the position of the vein changes from horizontal to vertical allowing gravity to exert it's effect decreasing the vein's transmural pressure which becomes negative and the vein collapses.

Dr. El-Shafei conducted experiments to study the role of collapse of the internal jugular vein in regulating the venous back flow from the brain during changes in posture [Ismail L. El Shafei, et al., "*Ventriculo-Jugular Shunt Against the Direction of Blood Flow, I. Role of the Internal Jugular Vein as an Antisiphonage Device*", Childs Nervous System, 3:282-284 (1987)]. He found that the internal jugular vein collapsed gradually, in a specific pattern, during change of posture from recumbent to erect. Collapse of the vein started at its upper end and proceeded downward with the increase in the angle of elevation of the cranium above the heart. The degree and extent of collapse of the vein varied according to the degree of elevation of the cranium; the more the cranium was elevated the more the vein collapsed. This phenomenon is similar to what happens to the veins on the dorsum of the hand when it is elevated. Collapse of the vein decreased it's capacity and increased the resistance to blood flow in it, counteracting the gain in pressure head due to elevation of the cranium. The increase in resistance to blood flow due to collapse of the vein was exactly equal to the gain in pressure head due to elevation of the cranium, so that the rate of venous back flow from the brain as well as all the intracranial pressures, i.e. the dural sinus pressure, the cerebral venous pressure and the cerebrospinal fluid pressure, remained constant and were not affected by gravity during the change of posture from recumbent to erect. In other words, collapse of the internal jugular vein on assuming the erect posture acted as a natural, precise and self regulating siphon control mechanism. Accordingly, Dr. El-Shafei concluded that: "any cerebrospinal fluid shunt for treatment of hydrocephalus should deliver the cerebrospinal fluid into the upper end of the internal jugular vein or into one of the dural sinuses in order to utilize the natural phenomenon of collapse of the internal jugular vein on assuming the upright body position to prevent siphonage".

Second Conclusion

Figure 1A:
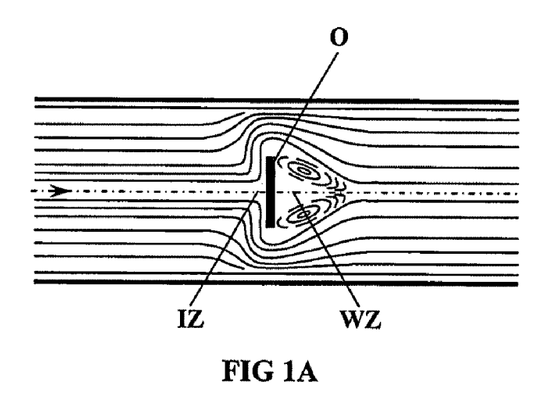
FIG. 1A is a diagrammatic illustration of the effects of placement of an obstacle in the way of a running stream.

The second conclusion was based on general hydraulic principles. In any ventriculo-venous shunt, the intra-venous portion of the shunting catheter constitutes an obstacle in the way of the running blood stream. According to hydraulic principles, placement of an obstacle in the way of a running stream induces changes in the pattern of flow and in the distribution of pressures inside the stream [W. L. McCabe, J. C. Smith, *Unit Operations of Chemical Engineering*, $2^{nd}$ Edition, Ch. 3 "Fluid-flow Phenomena", (1967) pp 47-67]. These changes are well known to hydraulic and aviation engineers. An impact zone will be created on the upstream side of the obstacle and a wake zone will be created on its downstream side (FIG. 1A). In the impact zone, the running fluid hits the obstacle, deflects and moves on, i.e. the fluid never stagnates in the impact zone, and is continuously renewed, while in the wake zone, some of the fluid separates from the streamlines and stagnates. Also, in the impact zone, the static pressure of the running fluid increases by an amount known as the impact pressure, while in the wake zone it decreases by an amount known as the wake effect. (N.B. The magnitude of the impact pressure or wake effect is directly proportional to the square of the velocity of fluid flow and equals $V^2/2$ g, where V is the velocity of flow and g is the gravitational acceleration which is a constant equal to 981 cm/s$^2$).

Figure 1B:
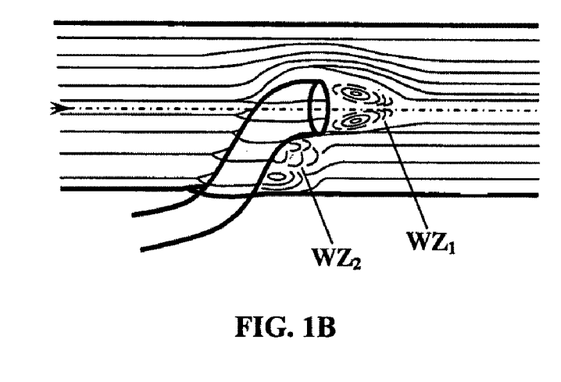
FIG. 1B is a diagrammatic illustration to show the sites of formation of wake zones when the shunting catheter is introduced into the venous channel in the direction of blood flow.

According to this hydraulic principle, if the shunting catheter of a ventriculo-venous shunt is introduced into the venous channel in the direction of blood flow (FIG. 1B), two wake zones will be created in the venous channel; one in front of the catheter's end ($WZ_1$ in FIG. 1B) and another at the axilla between the catheter and the wall of the venous channel ($WZ_2$ in FIG. 1B). At these sites, blood will stagnate and it's clotting will be encouraged (N.B. Blood clots when it stagnates, but not when it is continuously renewed). Also, in these wake zones, the static venous pressure will decrease by an amount equal to the wake effect of the blood stream. Accordingly, the intra-ventricular pressure will stabilize after shunt implantation, when it becomes equal to the wake zone pressure in front of the venous end of the shunting catheter, i.e. the stabilized intra-ventricular pressure will be less than the pressure in the draining venous channel by an amount equal to the wake effect of the blood stream; i.e. the normal relationship of the intraventricular pressure being more than the pressure in the draining venous channel will be reversed.

Figure 1C:
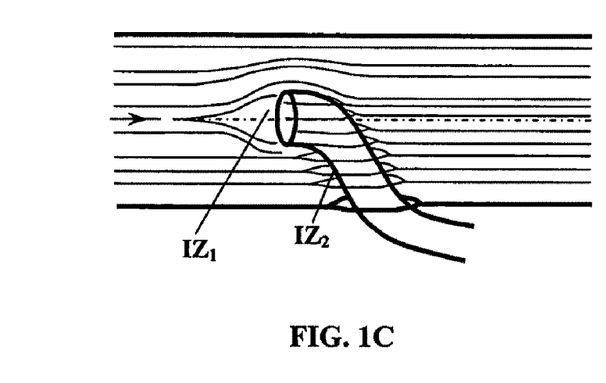
FIG. 1C is a diagrammatic illustration to show the sites of formation of impact zones when the shunting catheter is introduced into the venous channel against the direction of blood flow.

On the other hand, if the shunting catheter of a ventriculo-venous shunt is introduced into the venous channel against the direction of blood flow (FIG. 1C), two impact zones will be created in the venous channel, one in front of the catheter's venous end ($IZ_1$ in FIG. 1C) and another at the axilla between the catheter and the wall of the venous channel ($IZ_2$ in FIG. 1C). In the impact zones blood will never stagnate; it will be continuously renewed and its clotting will be discouraged. Also, the intraventricular pressure will stabilize after shunt implantation when it becomes equal to the impact zone pressure in front of the catheter's venous end, i.e., the stabilized intraventricular pressure after shunt implantation will be maintained more than the pressure in the draining venous channel by an amount equal to the impact pressure of the blood stream, preserving the relationship that normally exists between the two pressures. Accordingly, it was concluded that: "in order to discourage blood clotting at the venous end of a ventriculo-venous shunt and to normalize the intraventricular pressure and maintain it more than the pressure in the draining venous channel regardless of changes in posture or intra-thoracic pressure, the venous end of the shunting catheter should be introduced into the venous channel against the direction of blood flow and not in the direction of blood flow".

To sum up, on theoretical basis, Dr. El Shafei concluded that "a physiological way for treating hydrocephalus is to establish a closed watertight connection that will drain the excess cerebrospinal fluid from the cerebral ventricles and deliver it into the upper end of the internal jugular vein or into a dural sinus against the direction of blood flow, i.e. to implant a retrograde ventriculo-jugular or a retrograde ventriculo-sinus shunt". Such a treatment utilizes the collapse of the internal jugular vein in the erect posture to prevent siphonage, utilizes the impact pressure of the blood stream to maintain the normal relationship of the intra-ventricular pressure being more than the pressure in the draining venous channel regardless of changes in posture or intra-thoracic pressure and creates impact zones in the draining venous channel which discourage stagnation and clotting of blood at the venous end of the connection. This way of cerebrospinal fluid shunting mimics natural drainage of cerebrospinal fluid and eliminates almost all the predisposing factors for most of the problems and complications encountered after current shunting procedures. These theoretical conclusions needed confirmation.

Dr. El-Shafei et al. conducted experiments to study the dynamics of cerebrospinal fluid flow after implantation of retrograde ventriculo-jugular and retrograde ventriculo-sinus shunts respectively [Ismail L. El-Shafei and Mahmound A. El-Rifaii, "*Ventriculo-jugular shunt against the direction of blood flow. II Theoretical and experimental basis for shunting the cerebrospinal fluid against the direction of blood flow*", Child's Nervous System, (1987) 3:285-291 and Azza Mohamed Abdel Hamid El Shaarawy, "*Study of Alternative Methods for Cerebrospinal Fluid Shunting to the Venous Cir-* culation, Experimental Modeling", Thesis submitted to the Faculty of Engineering at Cairo University in partial fulfillment of the requirements for the degree of Doctor of Philosophy in Chemical Engineering, March 1997]. The results showed that after implantation of either of these shunts, provided that the ventriculo-venous connection is a closed system that does not allow leakage of cerebrospinal fluid, the intraventricular pressure will be regulated by its natural regulator, which is the pressure in the draining venous channel. The intra-ventricular pressure will be maintained within normal values at a level more than the pressure in the draining venous channel regardless of changes in posture or intra-thoracic pressure; therefore blood cannot regurgitate into a valveless shunting catheter as a result of these changes, flow of cerebrospinal fluid to the venous circulation will be continuous at a rate equal to and dependent upon the rate of its formation and siphonage will not develop when the upright body position is assumed. The results confirmed the theoretical conclusions and indicated that a valveless shunting catheter can be used to establish the retrograde ventriculo-venous connection. Reflux of blood into a valveless shunting catheter after implantation of a retrograde ventriculo-venous shunt can only occur if there is cerebrospinal fluid leakage, because loss of the cerebrospinal fluid will decrease the intra-ventricular pressure and make it less than the pressure in the draining venous channel. Therefore, injury to the dura mater should be avoided during shunt implantation and the dural hole made for shunt implantation should be hermetically sealed to prevent leakage from around the catheter. Also the shunt should be closed before attempting intradural surgical procedures and if a cerebrospinal fluid fistula develops. This is important because the dynamics of cerebrospinal fluid flow after implantation of retrograde ventriculo-venous shunts depend entirely on it's being a closed system allowing no leakage of cerebrospinal fluid.

During the $8^{th}$ and $9^{th}$ decades of the $20^{th}$ century, Dr. El-Shafei implanted retrograde ventriculo-jugular shunts to treat hydrocephalus [Ismail L. El-Shafei, "*Ventriculo-jugular shunt against the direction of bloodflow, III Operative technique and results*", Child's Nervous System, (1987) 3:342-349 and Ismail El-Shafei and Mohamed Ahmed Hafez, "*Ventriculo-jugular shunt against the direction of blood flow, IV Technical modifications and policy for treatment*", Child's Nervous System (1991) 7:197-204]. The results were satisfactory in patients above the age of 5 years. There were no problems related to improper cerebrospinal fluid drainage or blood clotting; confirming the validity of the theoretical conclusions and the experimental results. However, implantation of a retrograde ventriculo-jugular shunt was very difficult and quite often impossible in infants and young children due to the thin caliber of their neck veins. Also, when the shunt could be implanted in young patients, only a short segment of the shunting catheter could be introduced up into the thin internal jugular vein. Shortness of the intravenous catheter segment together with movements of the head and the rapid rate of longitudinal body growth in infants predisposed to slipping of the catheter out from the vein and cerebrospinal fluid leakage in the neck few months after shunt implantation. It became obvious that infants and young children are not suitable candidates for implantation of retrograde ventriculo-jugular shunts, and they were only implanted in patients above the age of 5 years.

During the last decade of the $20^{th}$ century, Dr. El Shafei, et al, implanted retrograde ventriculo-sinus shunts using valveless shunting catheters regardless of the patient's age [El Shafei I L, El Shafei H I, "*The retrograde ventriculo-sinus shunt. Concept and technique for treatment of hydrocephalus by shunting the cerebrospinal fluid to the superior sagittal sinus against the direction of blood flow. Preliminary report.* Childs' Nerv. Syst. 2001; 17:456-465, Ismail L El Shafei, Hassan I E L Shafei, "*The Retrograde Ventriculo-Sinus Shunt (El Shafei RVS Shunt). Rationale, Evolution, surgical technique and long term results.*" Pediatr Neurosurg 2005; 41:305-317]. The results were considered satisfactory, there were no problems related to improper cerebrospinal fluid drainage, siphonage, reflux of blood or blood clotting at the venous end of the connection. However, difficulties and problems were encountered during and after shunt implantation mainly due to cerebrospinal fluid leakage from around the shunting catheter because of imperfect sealing of the dural hole made for shunt implantation and difficulties in introducing the venous end of the connection into the sinus.

Conclusion: Since none of the available shunt systems possess features for hermetic sealing of the dural hole around the shunting catheter or for delivering the drained cerebrospinal fluid against the direction of blood flow in the sinus it became obvious that a specially designed shunt system is needed for easy and proper implantation of retrograde ventriculo-sinus shunts.

SUMMARY OF THE INVENTION

The aim of treatment for hydrocephalus is to return excess cerebrospinal fluid accumulating in the brain ventricles to the venous circulation in a way that normalizes the intraventricular pressure and avoids the problems and complications encountered after implantation of current cerebrospinal fluid shunts. Drs E L Shafei believe that "these objectives can be achieved by establishing a closed watertight connection between the cerebral ventricles and a dural sinus, e.g. the superior sagittal sinus or the transverse sinus, to drain excess cerebrospinal fluid from the brain ventricles and to deliver it into the dural sinus against the direction of blood flow in the sinus, i.e. to implant Retrograde Ventriculo-Sinus shunts". This way of cerebrospinal fluid shunting utilizes natural forces to normalize the intra-ventricular pressure, to prevent siphonage in the erect posture, to prevent reflux of blood as a result of changes in posture or intra-thoracic pressure, to maintain a continuous unidirectional flow of cerebrospinal fluid to the venous circulation and to discourage stagnation and clotting of blood at the venous end of the connection; hence, the need for incorporating flow control devices which are liable to failure and malfunction, i.e. check valves, differential pressure valves and programmable valves . . . etc., into shunting catheters is eliminated and a valveless shunting catheter may be used for shunt implantation, therefore:

A primary objective of this invention is to provide a shunt system for implantation of retrograde ventriculo-sinus shunts comprising: a shunting catheter to remove excess cerebrospinal fluid from the cerebral ventricles and to deliver it into a dural sinus against the direction of blood flow in the sinus such that no cerebrospinal fluid could leak from around the shunting catheter via the dural hole made for catheter insertion into the ventricle and a styforator for making a circular dural hole with a controlled diameter and for providing the axial force needed for introducing the ventricular end of the shunting catheter into the brain ventricle via the dural hole.

Another object of this invention is to provide a shunt system as above described wherein the shunting catheter is made of tissue compatible material suitable for implantation in patients, e.g. silicone rubber, consisting of a ventricular segment, an intermediate segment and a sinus segment in fluid continuity in the order mentioned. Such shunting catheter allows free flow of cerebrospinal fluid from the ventricles into the lumen of the catheter's ventricular segment to be conveyed via the catheter's intermediate segment to the catheter's sinus segment which delivers it into the sinus against the direction of blood flow in the sinus.

Another object of this invention is to provide a shunting catheter as above described wherein the ventricular segment is made of a high grade semi-rigid modulus silicone rubber resistant to bending or stretching, it's ventricular end is closed and inlet holes are circumferentially arranged in the wall of a short portion, e.g. 1.0 cm, of the catheter's main stem next to it's closed ventricular end; the intermediate segment is made of low grade bending modulus silicone rubber which is generally kink resistant, 3.0 cm beyond its beginning a 2.0 cms to 3.0 cms long side tube provided with a plug to close its open free end projects from its main stem, said side tube is directed toward the catheter's sinus end; and the sinus segment is 5.0 cms long, it's proximal half, i.e. next to the catheter's intermediate segment, is made of low grade bending modulus silicone rubber and it's distal half is made of high grade semi-rigid modulus silicone rubber that ends by a terminal circular sinus opening perpendicular to the longitudinal axis of the semi-rigid distal half.

Another object of this invention is to provide a shunting catheter as above described wherein the length of the ventricular segment is equal to the radiologically estimated distance between the dural hole made for catheter insertion into the ventricle and the site at which the catheter's ventricular end pierces the wall of the ventricle; the length of the intermediate segment is three times the distance between the site of the dural hole made for insertion of the catheter's ventricular end into the ventricle and the site of insertion of the catheter's sinus end into the sinus and the length of the sinus segment is about 5.0 cms.

Another object of this invention is to provide a shunting catheter as above described wherein the wall thickness of the catheter's three segments and of the side tube projecting from the intermediate segment is the same, the outer diameter of the catheter's ventricular segment is slightly less than the diameter of the dural hole made for catheter insertion into the ventricle and the outer diameter of the catheter's intermediate segment is slightly more than the diameter of the dural hole, the outer diameter of the side tube is similar to that of the ventricular segment and that of the sinus segment is 0.5 mm less than that of the ventricular segment.

Another object of this invention is to provide a shunt system as above described wherein the styforator is a 4.0 cms long stainless steel rod with a diameter slightly more than the outer diameter of the catheter's ventricular segment and slightly less than the outer diameter of the catheter's intermediate segment, one of it's ends tapers to form a 2.0 mms long cone with a sharp pointed perforating tip and from the center of it's other end projects a stylet whose diameter is slightly less than the inner diameter of the catheter's ventricular segment, it's length is three times the length of the catheter's ventricular segment and it's free end is bullet shape.

Another object of this invention is to provide a shunt system as above described having means for making a circular dural hole with a diameter slightly more than the outer diameter of the catheters ventricular segment and slightly less than the outer diameter of the catheter's intermediate segment. The means for making the desired dural hole in one embodiment takes the form of using the perforating end of the styforator to make the dural hole as will be described hereafter.

Another object of this invention is to provide a shunt system as above described having means for introducing the catheter's ventricular end into the ventricle. The means for introducing the catheter's ventricular end into the ventricle in one embodiment takes the form of introducing the stylet of the styforator into the catheter's ventricular segment so that it's bullet shaped tip rests against the catheter's closed ventricular end and provide the axial force needed for pushing the catheter's ventricular end into the ventricle.

Another object of this invention is to provide a shunting catheter as above described having means for introducing the stylet into the catheter's ventricular segment, for injecting fluids e.g. saline, into the ventricle or sinus and for recording the pressures in them during shunt implantation. The means for introducing the stylet into the ventricular segment, for injecting fluids and measuring pressures in one embodiment takes the form of the side tube projecting from the catheter's intermediate segment as will be described hereafter.

Another object of this invention is to provide a shunting catheter as above described having means for closing the side tube after shunt implantation. The means for closing the side tube in one embodiment takes the form of a plug to be introduced into the free end of the side tube and secured therein by a ligature just inside an annular ridge formed at the end of the plug.

Yet another object of this invention is to provide a shunting catheter as above described having means for allowing free flow of cerebrospinal fluid from the ventricle into the lumen of the catheter's ventricular segment. The means for allowing free flow of cerebrospinal fluid from the ventricle into the lumen of the catheter's ventricular segment in one embodiment takes the form of the inlet holes circumferentially arranged in the wall of a short portion of the catheter's ventricular segment next to its closed ventricular end.

A main object of this invention is to provide a shunting catheter as above described having means for hermetic sealing of the dural hole around the shunting catheter. The means for hermetic sealing of the dural hole in one embodiment takes the form of making the catheter's intermediate segment stretchable and with an outer diameter slightly more than the diameter of the dural hole so that during shunt implantation, the pre-side tube portion of the catheter's intermediate segment is stretched to make it thinner to allow passage of part of it through the dural hole when the catheter's ventricular end is well placed inside the ventricle, after which the catheter is released to allow it's stretched portion to recoil, regaining it's original diameter and snugly fitting in the dural hole hermetically sealing it.

Still another object of this invention is to provide a shunting catheter as above described having means for easy insertion of the catheter's sinus segment into the sinus and for maintaining it's direction against the direction of blood flow in the sinus. The means for easy insertion of the catheter's sinus segment into the sinus and for maintaining it's direction against the direction of blood flow in the sinus in one embodiment takes the form of making the terminal distal half of the sinus segment semi-rigid.

Yet another object of this invention is to provide a shunting catheter as above described having means for delivering the drained cerebrospinal fluid into the sinus against the direction of blood flow in the sinus. The means for delivering the cerebrospinal fluid into the sinus against the direction of blood flow in the sinus in one embodiment takes the form of making the terminal opening of the sinus segment circular and perpendicular to the longitudinal axis of the semi-rigid terminal half of the sinus segment (N.B. an oblique terminal opening for the sinus segment deprives the shunt from utilizing the benefit of the impact pressure of the blood stream in the sinus).

Another object of this invention is to provide a shunting catheter as above described having means for discouraging stagnation and clotting of blood at the venous end of the connection. The means for discouraging stagnation and clotting of blood in one embodiment takes the form of introducing the sinus segment of the shunting catheter into the sinus against the direction of blood flow in the sinus so as to create impact zones, which discourage stagnation and clotting of blood, instead of introducing it in the direction of blood flow which creates wakes zones that encourage stagnation and clotting of blood.

Another object of this invention is to provide a way for cerebrospinal fluid shunting having means to prevent the occurrence of siphonage in the erect posture. The means for preventing siphonage in the erect posture in one embodiment takes the form of delivering the drained cerebrospinal fluid into a dural sinus, i.e. proximal to the internal jugular vein, so as to utilize the natural phenomenon of collapse of the internal jugular vein in the erect posture to prevent siphonage.

Another object of this invention is to provide a way for cerebrospinal fluid shunting having means to normalize the intraventricular pressure, to maintain a continuous unidirectional flow of cerebrospinal fluid to the venous circulation at a rate equal to the rate of it's formation and to prevent regurgitation of blood into the shunting catheter as a result of changes in posture or intra thoracic pressure. The means for fulfilling the aforementioned objectives in one embodiment takes the form of delivering cerebrospinal fluid into the sinus against the direction of blood flow so as to utilize the impact pressure of the blood stream in the sinus to maintain the intraventricular pressure more than the dural sinus pressure regardless of changes in posture or intra-thoracic pressure.

With the above and other objects in view that may hereafter become apparent, the nature of the invention may be clearly understood by reference to the views illustrated in the accompanying drawings, the following detailed description thereof and the appended claimed subject material.

BRIEF DESCRIPTION OF THE DRAWINGS

FIG. 2 B is a magnified sectional elevation of the shunting catheter of the shunt system of this invention having portions thereof cut away.

LEGENDS TO THE FIGURES

O Obstacle
IZ Impact zone
WZ Wake zone
SC Shunting catheter
VS Ventricular segment
IS Intermediate segment
SS Sinus segment.
SF Styforator.
S Stylet.
P Perforator.
DM Dura mater.
DH Dural hole.
SSS Superior sagittal sinus.
TS Transverse sinus.
SR Sinus roof.
Lig Ligature.
1 Ventricular end of the shunting catheter.
2 Depression in the base of the catheter's ventricular end.
3 Inlet holes.
4 Main stem of ventricular segment.
5 Pre-side tube portion of the catheter's intermediate segment.
6 Marker line at the middle of the pre-side tube portion of the catheter's intermediate segment.
7 Side tube.
8 Plug for closure of the side tube.
9 Post side tube portion of the catheter's intermediate segment.
10 Proximal bendable half of the sinus segment.
11 Distal semi-rigid half of the sinus segment.
12 Terminal circular opening of the sinus segment.
13 Main stem of the styforator.
14 Tapering perforating free end of the styforator.
15 Bullet shaped free end of the stylet portion of the styforator.

DETAILED DESCRIPTION OF THE INVENTION

On theoretical, experimental and clinical basis it was concluded that a physiological way for treatment of hydrocephalus is to implant retrograde ventriculo-sinus shunts. Provided the connection is watertight allowing no leakage of cerebrospinal fluid, this way of cerebrospinal fluid shunting utilizes natural forces, to prevent siphonage in the erect posture, to prevent regurgitation of blood into the shunting catheter as a result of changes in posture or intra-thoracic pressure, to normalize the intra-ventricular pressure, to maintain a steady unidirectional flow of cerebrospinal fluid to the venous circulation at a rate equal to the rate of it's formation and to discourage stagnation and clotting of blood at the sinus end of the connection. Therefore, a valveless shunting catheter can be used to establish the connection and the need to incorporate artificial flow control devices into shunting catheters is eliminated. Thus, the first innovation is to utilize natural forces instead of artificial devices that are liable to failure and malfunction to regulate the dynamics of flow of cerebrospinal fluid in shunt systems.

A second innovation is to hermetically seal the dural hole made for shunt implantation to prevent leakage of cerebrospinal fluid from around the shunting catheter, unlike what happens when current cerebrospinal fluid shunts are implanted where the dura mater is opened by a cruciate incision and no attempt is made to seal it around the catheter.

A third innovation is to introduce the venous end of the shunting catheter into the dural sinus against the direction of blood flow in it so as to create impact zones that discourage stagnation and clotting of blood rather than introducing it in the direction of blood flow as is currently done, which creates wake zones that encourage stagnation and clotting of blood.

A fourth innovation is to deliver the drained cerebrospinal fluid into the dural sinus against the direction of blood flow in it in order to utilize the impact pressure of the blood stream in the sinus to maintain the intraventricular pressure more than the dural sinus pressure regardless of changes in posture or intra-thoracic pressure.

Figure 4:
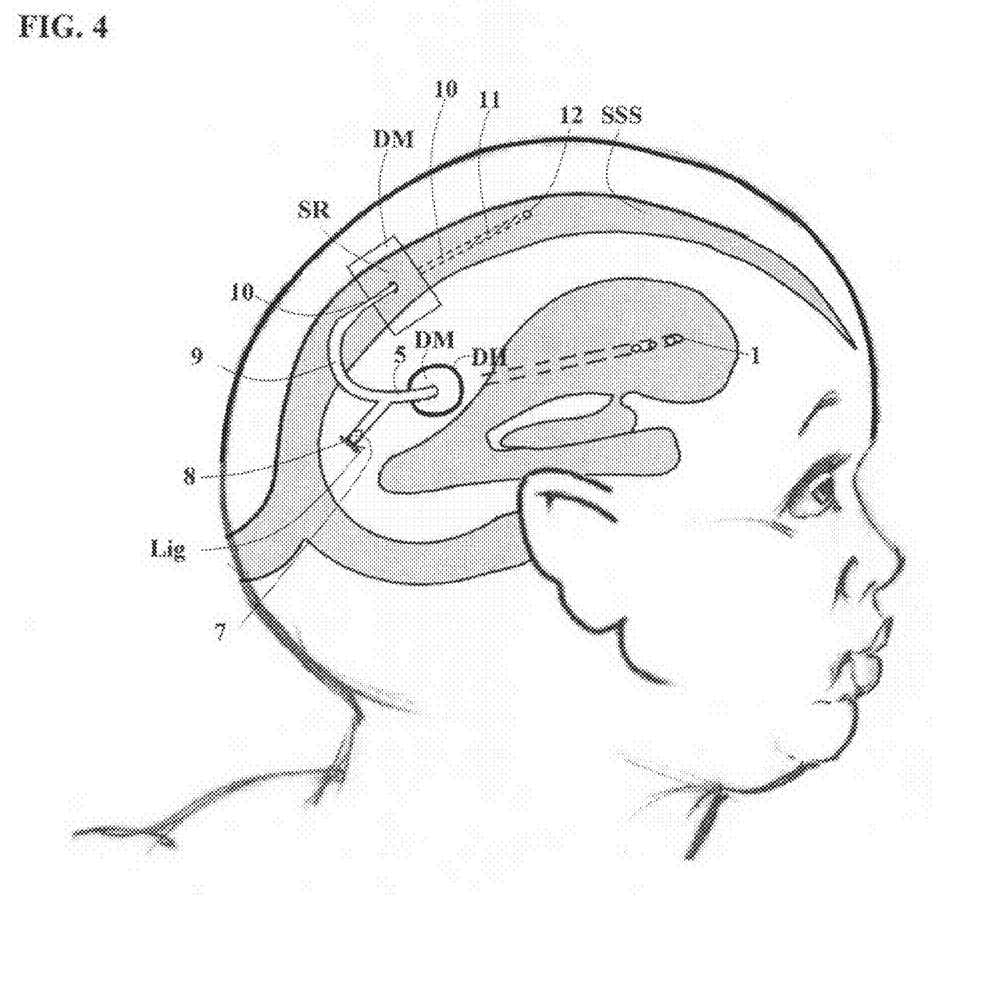
FIG. 4 is a diagrammatic illustration to show the shunting catheter of the shunt system of this invention implanted in a hydrocephalic patient to establish a retrograde ventriculo superior sagittal sinus shunt.

As is shown in the drawings for purposes of illustration, the present invention is concerned with a shunt system for implantation of retrograde ventriculo-sinus shunts. The following is a description of a preferred embodiment for a shunt system that may be used in an adult patient for implantation of a retrograde ventriculo-superior sagittal sinus shunt to drain cerebrospinal fluid from the anterior horn of the lateral ventricle and to deliver it against the direction of blood flow in the posterior third of the superior sagittal sinus (FIG. 4). This is the preferred route for shunt implantation unless otherwise indicated. Other routes may be preferred according to the age of the patient, the degree of ventricular dilatation, the size of the dural sinuses and the condition of the scalp. Naturally, the construction, configuration and dimensions of shunt components will differ according to the age of the patient and according to the route chosen for shunt implantation. However, the invention is not limited to the details of construction and measurements described in the text or illustrated in the accompanying drawings; these are exemplary dimensions. The invention is capable of other embodiments and of being performed in other ways, also the catheter may be made in one piece or in two pieces to be joined together during shunt implantation. Many changes can be made in the construction, configuration and measurements of components to suit different ages and different routes chosen for shunt implantation without departing from the scope of the invention.

In a preferred embodiment, the shunt system of this invention comprises a valveless shunting catheter and a styforator designated with the letters SC and SF respectively, reference numbers designate the components of each of them.

Figure 2A:
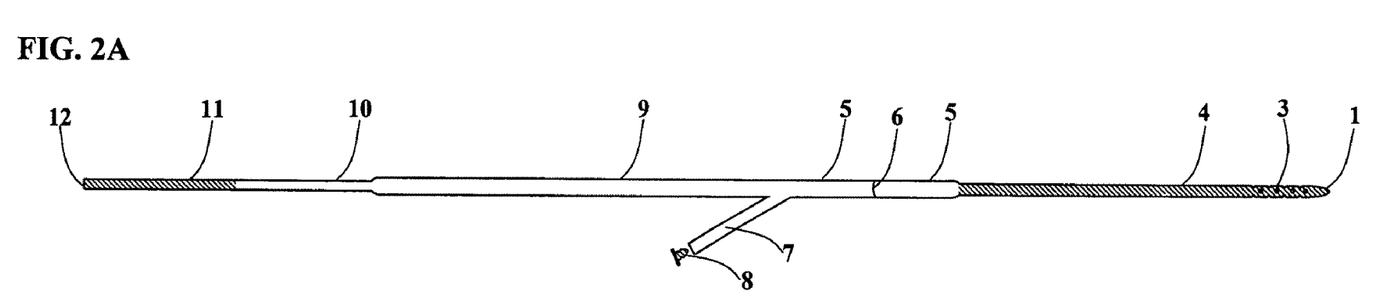
FIG. 2A is a plan view of the shunting catheter of the shunt system of this invention.
Figure 2B:
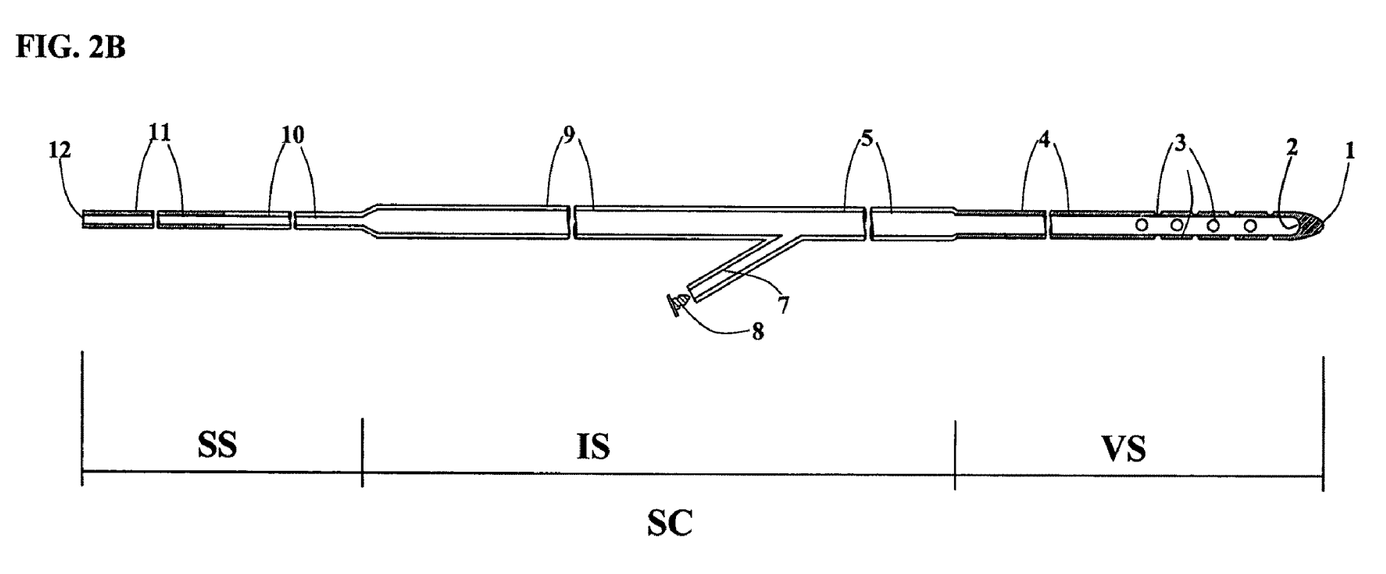

The Shunting Catheter (FIGS. 2A & B):

It's made of tissue compatible material e.g. silicone rubber. It's length varies according to the age of the patient and to the route chosen for shunt implantation; for the described embodiment, the length of the shunting catheter may be about 22.0 cms. For purposes of description the catheter may be divided into three segments: a ventricular segment, an intermediate segment and a sinus segment in fluid continuity in the order mentioned, designated with the letters VS, IS and SS respectively, wherein:

The ventricular segment (VS) (FIGS. 2A & B), is made of implant grade high semi-rigid modulus silicone rubber resistant to bending or stretching. It's length is equal to the radiologically estimated distance between the site of the dural hole made for catheter insertion into the ventricle and the site of passage of the catheter's ventricular end 1 through the wall of the ventricle; for the described embodiment it's length is about 6.0 cms. It's outer diameter is slightly less than the diameter of the dural hole made for shunt implantation; for the described embodiment the outer and inner diameters may be 2.2 mm and 1.0 mm respectively. It's ventricular end 1 is a 0.5 cm long cone of catheter material whose apex forms the tip of the catheter's ventricular end 1 and whose base closes the ventricular end of the lumen of the catheter's ventricular segment. There is a depression 2 in the center of the base of the catheter's ventricular end 1 to lodge a bullet shaped tip 15 of the stylet S, which is used to provide the axial force needed for pushing the catheter's ventricular end 1 into the ventricle during shunt implantation. Inlet holes 3, to allow free flow of cerebrospinal fluid from the ventricle into the lumen of the catheter's ventricular segment, are circumferentially arranged in the wall of a short portion e.g. 1.0 cm of this segment's main stem 4 next to the catheter's ventricular end 1. The main stem 4 of the catheter's ventricular segment extends for about 5.0 cms beyond inlet holes 3 to join in fluid continuity the proximal pre-side tube portion 5 of the main stem of the catheter's intermediate segment.

The intermediate segment (IS) (FIGS. 2A & B), is made of implant grade low bending modulus silicone rubber, which is generally stretchable and kink resistant. It's length varies according to the age of the patient and the route chosen for shunt implantation and is about three times the distance between the dural hole made for catheter insertion into the ventricle and the site for insertion of the catheter's sinus end into the sinus; for the described embodiment it's length is about 10.0 cms; it's outer diameter is slightly more than the diameter of the dural hole made for insertion of the catheter's ventricular end 1 into the ventricle; for the described embodiment the outer and inner diameters of the intermediate segment are 3.0 mm and 1.8 mm respectively i.e. 0.8 mm more than those of the catheter's ventricular segment. A side tube 7 projects from the segment's main stem 3.0 cm beyond it's beginning, having outer and inner diameters equal to those of the catheter's ventricular segment. Side tube 7 is directed towards the catheter's sinus end, making an acute angle 30° with the catheter's main stem. Side tube 7 is provided with a plug 8 to close it at the end of the procedure for shunt implantation. There is a marker line 6 at the middle of the pre-side tube portion 5 of the catheter's intermediate segment. The main stem of the intermediate segment extends beyond the side tube 7 as a post side tube portion 9 for a variable distance according to the age of the patient and route chosen for shunt implantation to join in fluid continuity the proximal bendable half 10 of the catheter's sinus segment; for the described embodiment the length of the post side tube portion 9 is about 7.0 cms.

The sinus segment (SS) (FIGS. 2A & B). It's dimensions vary according to the age of the patient, the size of the sinus and the site chosen for shunt implantation; for the described embodiment it's length is 5.0 cms with outer and inner diameters 1.7 mm and 0.5 mm respectively. When the shunt is implanted the sinus segment lies mainly in the sinus; it's object is to facilitate insertion of the sinus segment into the sinus, to maintain the direction of the sinus segment against the direction of blood flow in the sinus and to deliver the drained cerebrospinal fluid into the sinus against the direction of blood flow; it's outer and inner diameters are less than those of the catheter's ventricular segment by 0.5 mm each. It's proximal half 10, i.e. the 2.5 cms next to the post side tube portion 9 of the catheter's intermediate segment, is made of implant grade low bending modulus silicone rubber while it's distal terminal half 11 is made of a higher grade durometer semi-rigid modulus silicone rubber that resist bending so as to facilitate insertion of the catheter's sinus segment into the sinus and to maintain the direction of the sinus segment against that of blood flow in the sinus. It's terminal sinus opening 12 is circular and perpendicular to the longitudinal axis of the terminal semi-rigid portion 11 of the sinus segment so as to deliver the drained cerebrospinal fluid into the sinus against the direction of blood flow in the sinus. (N.B. an oblique terminal sinus opening deprives the shunt from the benefit of utilizing the impact pressure of the blood stream in the sinus to maintain the intraventricular pressure more than the sinus pressure)

Figure 3:
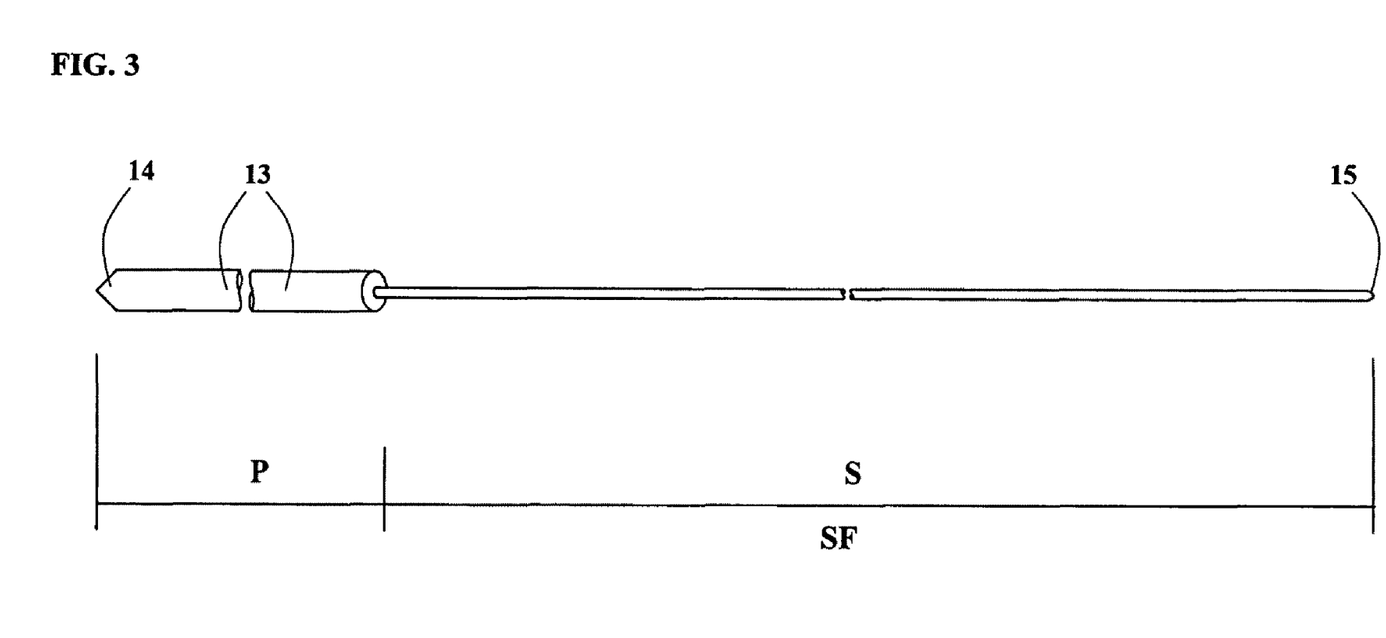
FIG. 3 is a magnified plan view of the styforator of the shunt system of this invention having portions thereof cut away.

The Styforator (SF) (FIG. 3):

It is made of stainless steel; it is used for making a circular dural hole with a controlled diameter slightly more than the outer diameter of the catheter's ventricular segment and slightly less than the outer diameter of the catheter's intermediate segment and for providing the axial force needed for insertion of the catheter's ventricular end 1 into the ventricle.

For the described embodiment the main stem 13 of the styforator is a 4.0 cms long rod with a diameter 2.5 mms; one of it's ends 14 tapers to form a 2.0 mms long cone with a sharp perforating tip and from the center of it's other end projects stylet S whose length is three times the length of the catheter's ventricular segment and it's diameter is slightly less than the inner diameter of the catheter's ventricular segment; for the described embodiment the length of the stylet S is 18.0 cms and it's diameter is 0.8 mm. The free end 15 of the stylet is bullet shaped.

FIG. 4 is a diagrammatic illustration of the shunting catheter of the shunt system of this invention implanted to establish a retrograde ventriculo-superior sagittal sinus shunt; the steps for shunt implantation are:

Exposing the sites chosen for insertion of the catheter's ventricular and sinus ends into the ventricle and sinus respectively: for the described illustration a posterior parietal scalp flap is reflected backward to expose 1.5 cm of the roof of the superior sagittal sinus 10.0 cm to 12.0 cm anterior to the external occipital protuberance and a 1.5 cm circle of dura mater lateral to the site for exposure of the sinus roof.

Making the dural hole: a weak diathermy current is passed through the styforator whose perforating tip 14 is lightly pressing on the center of the exposed dura mater. The perforating tip 14 of the styforator will pierce the dura mater, coagulating the margin of the perforation whose diameter will increase gradually until the main stem 13 of the styforator enters the perforation making a circular dural hole with a diameter equal to that of the styforator's main stem 13, i.e. slightly more than the outer diameter of the catheter's ventricular segment and slightly less than the outer diameter of the catheter's intermediate segment.

Insertion of the catheter's ventricular end 1 into the ventricle: the stylet S is introduced into the catheter's ventricular segment via side tube 7 and is advanced until it's bullet shaped tip 15 lodges in depression 2 in the base of the catheter's ventricular end 1. The catheter is stretched over the stylet; this will stretch the pre-side tube portion 5 of the catheter's intermediate segment making it thinner to allow it's passage through the dural hole. The catheter's ventricular end 1 is introduced into the anterior horn of the lateral ventricle by passing it through the dural hole and pushing it in the direction of the ipsilateral pupil until the catheter's ventricular end 1 enters the ventricle and until marker line 6, at the middle of the pre-side tube portion 5 of the catheter's intermediate segment reaches the dural hole. At this point the position of the stylet is fixed to maintain the position of the catheter's ventricular end 1 into the ventricle and the catheter is released gradually to allow the stretched pre-side tube portion 5 to relax and recoil pulling another part of the pre-side tube portion 5 intradurally and marker line 6 will disappear through the dural hole. After releasing the stretched catheter the stylet is removed. Relaxation of the stretched pre-side tube portion 5 will allow it to regain it's original diameter, fitting snugly in the dural hole and hermetically sealing it.

Confirming proper sealing of the dural hole: since the dynamics of flow in the retrograde ventriculo-sinus shunt depend entirely on it's being a closed system that allows no leakage of cerebrospinal fluid, a tissue adhesive, e.g. Histoacryle blau or fibrin glue, is applied to stick the outer surface of the extradural part of the pre-side tube portion 5 of the catheter's intermediate segment to the outer surface of the dura mater surrounding the dural hole. After solidification of the tissue adhesive, a bulldog clamp is applied on the post side tube portion 9 of the catheter's intermediate segment and saline is injected into the ventricle via side tube 7 to replace lost cerebrospinal fluid and to raise the intraventricular pressure to make sure there is no leakage of cerebrospinal fluid from around the shunting catheter. Another bulldog clamp is applied on the extradural part of the pre-side tube portion 5 of the catheter's intermediate segment to maintain the high intraventricular pressure and the bulldog clamp on the post side tube portion 9 is removed.

Insertion of the catheter's sinus segment into the sinus: Saline is injected via side tube 7 to fill the catheter's intermediate and sinus segments with saline and to drive air out from them. A small hole is made in the center of the exposed sinus roof by passing a weak diathermy current through the stem of the stylet S whose tip 15 is lightly pressing on the sinus roof. Bleeding from the sinus is controlled by applying a finger on the hole. The sinus end 12 of the terminal sinus segment's semi-rigid portion 11 is introduced into the sinus and is advanced forward against the direction of blood flow for a suitable distance. Bleeding from around the catheter is controlled by gel foam. Saline is injected via side tube 7 to make sure it's flow to and in the sinus is free.

Recording pressures: a manometer filled with saline is connected to the catheter's side tube 7. The saline in the manometer falls down and when it stabilizes the sinus pressure is recorded. A bulldog clamp is applied on the post side tube portion 9 of the catheter's intermediate segment and the manometer is refilled with saline; the clamp on the extradural part of the pre-side tube portion 5 of the catheter's intermediate segment is removed. The saline in the manometer falls down and when it stabilizes the initial intraventricular pressure is recorded (N.B. if the intraventricular pressure is found low, as a result of cerebrospinal fluid loss during shunt implantation, saline is injected into the ventricle to raise the intraventricular pressure above the recorded sinus pressure to provide a pressure head to initiate flow from the ventricle to the sinus once free flow is allowed in the shunting catheter). The bulldog clamp on the post side tube portion 9 of the catheter's intermediate segment is removed allowing free flow in the shunting catheter. The saline in the manometer falls down gradually and when it stabilizes the stabilized intraventricular pressure after shunt implantation is recorded.

Wound closure: after recording the pressures, the manometer is removed and plug 8 is fitted in the free open end of side tube 7 and is secured in place by a ligature (Lig. in FIG. 4). The extra-cranial intermediate segment is laid in a smooth curve in a subgaleal pocket formed behind the base of the skin flap and the wound is closed.

After shunt implantation cerebrospinal fluid will flow from the ventricle where the pressure is high to the dural sinus where the pressure is less until equilibrium between the pressures in the two compartments is achieved after which the impact pressure of the blood stream in the sinus will maintain the intraventricular pressure more than the sinus pressure and as long as this relationship is maintained, blood can not regurgitate into the shunting catheter as a result of changes in posture or intra-thoracic pressure and a continuous unidirectional flow of cerebrospinal fluid from the ventricle to the sinus will be maintained at a rate equal to and dependent on it's rate of formation. Insertion of the catheter's sinus segment into the sinus against the direction of blood flow will create impact zones in the sinus which discourage stagnation and clotting of blood at the venous end of the connection. Also, delivering the drained cerebrospinal fluid into a dural sinus, i.e. proximal to the internal jugular vein, prevents siphonage in the erect posture by utilizing the natural phenomenon of collapse of the internal jugular vein in the erect posture.

Having described the invention, what is claimed is:

1. A shunt system for implantation of retrograde ventriculo-sinus shunt comprising a shunting catheter and a styforator wherein:

the shunting catheter is made of tissue compatible material suitable for implantation in patients, consisting of a ventricular segment, an intermediate segment, and a sinus segment in fluid continuity in the order mentioned wherein:

the ventricular segment is made of a high grade semi-rigid modulus silicone rubber resistant to bending and stretching, having a length configured to span the distance between a dural hole made for insertion of the catheter's ventricular end into the ventricle and the site at which the catheter's ventricular end pierces the wall of the ventricle, having a diameter configured to fit into a circular dural hole made for insertion of the catheter's ventricular end into the ventricle, wherein the ventricular end is closed and inlet holes are circumferentially arranged in the wall of a short portion, of its closed ventricular end;

the intermediate segment is made of low grade bending modulus silicone rubber which is generally kink resistant, having a length about three times the distance between the circular dural hole made for insertion of the catheter's ventricular end into the ventricle and the site for insertion of the catheter's sinus end into the roof of the dural sinus, wherein the outer and inner diameters of the intermediate segment are more than those of the catheter's ventricular segment by 1.0 mm each, the outer diameter being slightly more than the diameter of the circular dural hole made for insertion of the catheter's ventricular end into the ventricle, the intermediate segment further comprising a 2.0 to 3.0 cm long side tube, having outer and inner diameters equal to those of the catheter's ventricular segment projecting from the intermediate segment's main stem about 3.0 cms distal the proximal end of the intermediate segment, said side tube is angled towards the catheter's sinus end and is provided with a plug to close its open free end, further comprising a marker line at the middle of the pre-side tube portion of the intermediate segment's main stem wherein the tube portion of the intermediate segment has a length configured to join tube portion extends to join in fluid continuity the proximal end of the catheter's sinus segment;

the sinus segment is about 5.0 cms long, with outer and inner diameters less than those of the catheter's ventricular segment by 0.5 mm each, the sinus segment's proximal half is made of low grade bending modulus silicone rubber while its distal terminal half is made of a higher grade durometer semi-rigid modulus silicone rubber, wherein the sinus segment ends as a circular terminal sinus opening perpendicular to the longitudinal axis of the terminal semirigid half of the sinus segment;

the styforator is made of stainless steel, it is a 4.0 cms long cylindrical rod with a diameter configured to be slightly larger than the outer diameter of the catheter's ventricular segment and slightly less than the outer diameter of the catheter's intermediate segment, one of its ends tapers to form a 2.0 mm long cone with a sharp pointed perforating tip while from the center of its other end projects a stylet configured to have a length three times the length of the catheter's ventricular segment having a diameter slightly less than the inner diameter of the catheter's ventricular segment and wherein the styforator's free end is bullet shaped.

2. A method for implanting retrograde ventriculo-sinus shunts using shunt systems according to claim 1 comprising the steps of:

exposing a patient's dura mater and sinus roof at sites chosen for insertion of the catheter's ventricular and sinus ends into the ventricle and sinus respectively;

making a circular dural hole with the styforator in the center of the exposed dura mater;

introducing the stylet of the styforator into the catheter's ventricular segment;

stretching the pre-side tube portion of the catheter's intermediate segment over the stylet;

introducing the catheter's ventricular end into the ventricle and advancing it until the marker line at the middle of the stretched pre-side tube portion of the catheter's intermediate segment reaches the dural hole;

releasing the catheter to allow the stretched pre-side tube portion of the catheter's intermediate segment to recoil and regain its original diameter while fitting snugly in the dural hole, thereby hermetically sealing the hole;

removing the stylet;

injecting saline via the catheter's side tube into the ventricle to raise intraventricular pressure and applying a bulldog clamp on the extra-dural part of the pre-side tube part of the catheter's intermediate segment to maintain the high intraventricular pressure;

making a small circular hole in the center of the exposed sinus roof;

introducing the free sinus end of the semi-rigid distal half of the catheter's sinus segment into the sinus and advancing it for a suitable distance against the direction of blood flow in the sinus;

closing the catheter's side tube with its plug;

removing the bulldog clamp on the pre-side tube portion of the catheter's intermediate segment;

placing the extra-cranial portion of the catheter's intermediate segment in a subgaleal pocket;

and closing the wound.

* * * * *